United States Patent [19]

Nakai et al.

[11] Patent Number: 4,697,590
[45] Date of Patent: Oct. 6, 1987

[54] APPARATUS FOR TREATING ATHLETE'S FOOT

[75] Inventors: Kimimoto Nakai; Isao Umezaki, both of Kanazawa, Japan

[73] Assignee: Shibuya Kogyo Co., Ltd., Kanazawa, Japan

[21] Appl. No.: 811,620

[22] Filed: Dec. 20, 1985

[30] Foreign Application Priority Data

Dec. 24, 1984 [JP] Japan .................. 59-195602[U]
Dec. 28, 1984 [JP] Japan .................. 59-199185[U]

[51] Int. Cl.$^4$ ............................................ A61N 5/06
[52] U.S. Cl. ................................. 128/396; 362/401
[58] Field of Search ............... 128/303.1, 395, 396; 248/364, 280.1, 162.1; 362/401

[56] References Cited

U.S. PATENT DOCUMENTS

| | | | |
|---|---|---|---|
| 3,467,098 | 9/1969 | Ayres | 128/395 X |
| 3,528,424 | 9/1970 | Ayres | 128/303.1 |
| 3,703,176 | 11/1972 | Vassiliadis et al. | 128/395 |
| 3,913,582 | 10/1975 | Sharon | 128/303.1 |
| 4,473,074 | 9/1984 | Vassiliadis | 128/395 X |
| 4,580,557 | 4/1986 | Hertzmann | 128/303.1 |

Primary Examiner—Anton O. Oechsle
Attorney, Agent, or Firm—Thomas S. MacDonald; Alan H. MacPherson; Paul J. Winters

[57] ABSTRACT

A laser-applied treatment apparatus includes a TEA type laser unit and a flexible link, such as a multi-joint arm assembly, for leading a laser beam emitted from the laser unit to a desired location, such as a part of a person's skin which is affected by dermatophytosis, in any desired orientation. Also provided is a pair of convex and concave lenses in the optical path of the apparatus for narrowing and collimating the laser beam such that it has an energy density suitable for use in treatment, e.g., athlete's foot. In one embodiment, a hand switch is mounted on a hand piece portion of the flexible link, and it controls the operation of the laser unit. Also provided is a foot switch which is operatively associated with the hand switch such that the operation of the first switch is rendered valid as long as the foot switch is kept depressed. Such a double switch structure provides an advantageous safety feature.

8 Claims, 5 Drawing Figures

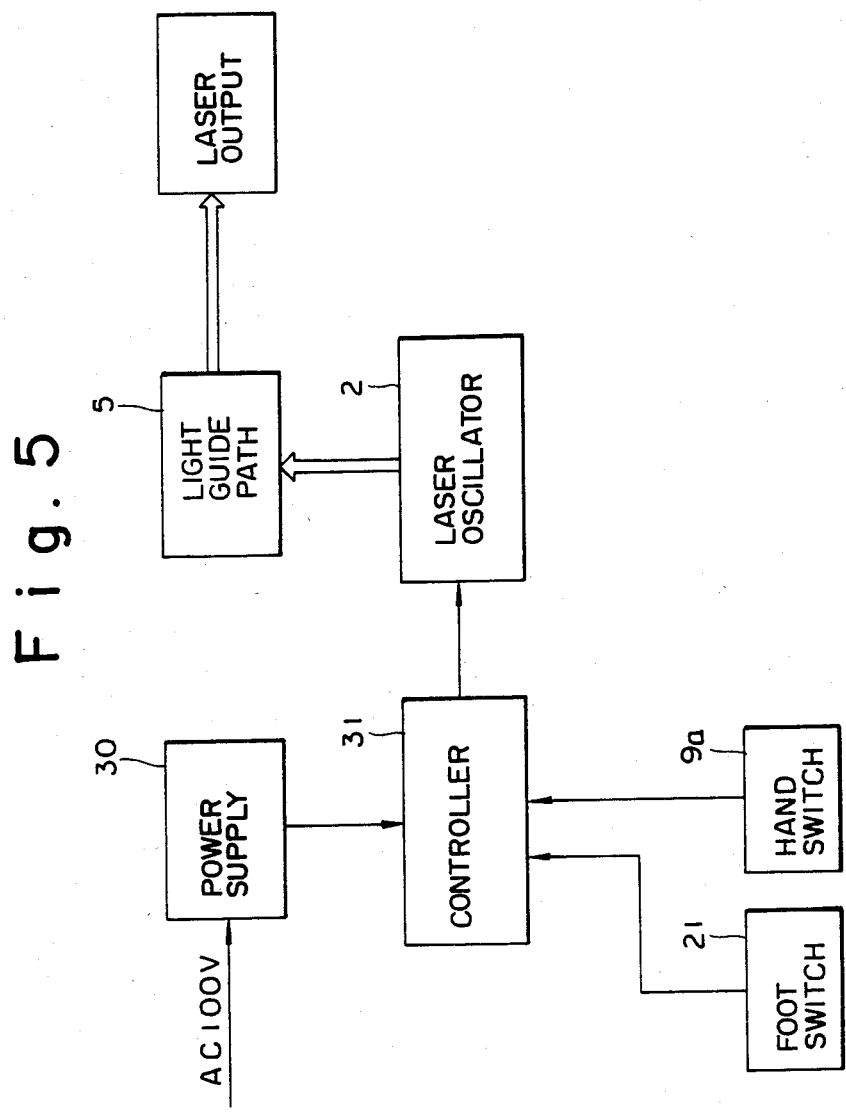

APPARATUS FOR TREATING ATHLETE'S FOOT

RELATED APPLICATION

This application is related to U.S. Ser. No. 603,543, now U.S. Pat. No. 4,640,283, entitled: "METHOD OF CURING ATHLETE'S FOOT BY LASER BEAM IRRADIATION", which is incorporated herein by reference. Said application has a common assignee with the present application.

BACKGROUND OF THE INVENTION

1. Field of the Invention

This invention generally relates to laser-applied medical apparatuses, and in particular, to an apparatus for treating athlete's foot using a laser beam having a controlled energy level.

2. Background of the Invention

It has been proposed to treat athlete's foot with the irradiation of a laser beam having a predetermined energy level for a predetermined time period to the above-related U.S. counterpart of area of a person's skin affected by dermatophytosis as disclosed in the Japanese Patent Application, No. 58-239563, the foreign priority document of said related application, which has been assigned to the assignee of this application and is hereby incorporated by reference. The method of treatment of athlete's foot using a laser beam disclosed in the above-identified application is based on the fact that ringworms only live in the epidermis or the surface layer of the skin, and more specifically in the stratum corneum or stratum corneum layer, which is the outermost layer of the epidermis. Heat-sensitive nerves extend up to the corium or the true skin and they do not extend into the stratum corneum layer. If irradiation of a laser beam having an energy density of a predetermined amount or more is momentarily carried out to the affected part of skin for a predetermined time, the stratum corneum layer can be heated to a temperature suitable for the treatment of athlete's foot, e.g., 70° C. or more, while maintaining the temperature of the true skin where heat-sensitive nerves exist, not causing any burn to the true skin.

Described more in detail, as long as an irradiation of a laser beam is such that the laser beam has an appropriate magnitude of energy density and is momentary and limited to a predetermined time duration or less, even if the stratum corneum layer is heated to a temperature effective to kill the ringworms living therein, the heat thus produced in the stratum corneum layer is effectively dissipated through the skin so that the temperature substantially drops to a low level by the time in which the heat reaches the heat-sensitive nerves in the true skin thereby preventing the patient from feeling heat. Accordingly, in order to relieve the patient from feeling heat during treatment, it is necessary that heating due to irradiation of the laser beam take place only at the surface of the epidermis, or more preferably within the stratum corneum layer, and not in the true skin. With such heating, an excellent treatment of athlete's foot can be carried out without causing the patient to feel heat.

Under the circumstances, in accordance with the above-identified application, it has been proposed to treat athlete's foot by the application of one or more irradiations of a laser beam having an energy density of 2 Joules/cm$^2$ or more in a time period of 10 milliseconds or less to a part of the body affected by dermatophytosis. The treatment of athlete's foot with a laser beam would not require significant endurance of heat by the patient.

It is to be noted, however, that it is not only the foot of a body which can be affected by dermatophytosis, but also other parts of the body, such as hands, are also liable to be infected. Moreover, when the roots of fingers or toes are infected, the application of a laser beam having a predetermined energy level to such parts of a body is extremely difficult. Thus, a need exists for an apparatus which can apply a controlled laser beam to any part of a body freely without restrictions, thereby completely curing that part of the body which is affected by dermatophytosis. In addition, since a laser unit is inherently a high-power device, it is desirous that some kind of a safety feature be provided to terminate the treatment operation if the apparatus malfunctions for some reason.

SUMMARY OF THE INVENTION

It is therefore a primary object of the present invention to obviate the disadvantages of the prior art as described above and to provide a novel apparatus for applying a controlled laser beam to a desired part of a body.

Another object of the present invention is to provide an apparatus for applying a laser beam, which includes a multi-joint light-guide arm for guiding a laser beam emitted from a laser unit to a desired part of a body.

A further object of the present invention is to provide an apparatus for treating athlete's foot using a laser beam having a predetermined energy level.

A still further object of the present invention is to provide an apparatus for applying a controlled laser beam for treatment of a skin of a person's body.

Other objects, advantages and novel features of the present invention will become apparent from the following detailed description of the invention when considered in conjunction with the accompanying drawings.

BRIEF DESCRIPTION OF THE DRAWINGS

FIG. 5 is a block diagram showing the overall structure of a control system incorporated in the apparatus.

DESCRIPTION OF THE PREFERRED EMBODIMENTS

Figure 1:
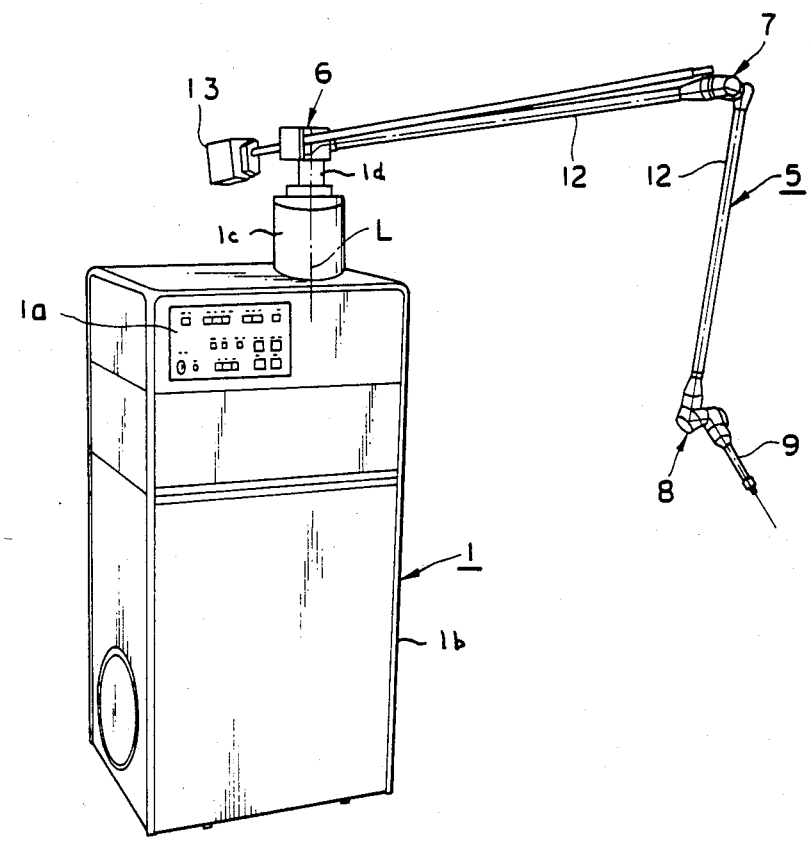
FIG. 1 is a schematic, perspective view showing an apparatus for applying a controlled laser beam having a multi-joint arm constructed in accordance with one embodiment of the present invention.

Referring now to FIG. 1, there is schematically shown a laser-applied treatment apparatus 1 which is constructed in accordance with one embodiment of the present invention so as to apply a controlled laser beam to a desired part of a body, such as a human body. As shown, the apparatus 1 includes a housing 1b which contains therein a laser unit 2 (not shown in FIG. 1, but shown in FIG. 2) as arranged vertically. Preferably, use is made of a pulsed, $CO_2$ TEA type laser as the laser unit 2. A control panel 1a, including a plurality of switches and indicator lamps, is mounted on the front surface of the housing. As indicated by the one-dotted line L in FIG. 1, a laser beam emitted from the laser unit 2 contained in the housing 1b is emitted vertically upward to a support projection 1c fixedly mounted on top of the housing 1b. The support projection 1c includes a support rod 1d which projects vertically upward from and is rotatable with respect to the support projection 1c and which supports a multi-joint arm assembly 5, which functions to guide the laser beam L supplied from the laser unit 2 in the housing 1b to a desired location, such as a part of a body infected by dermatophytosis, so as to be movable in any direction.

In the illustrated embodiment, the multi-joint arm assembly 5 includes three joints 6 through 8 and three straight arms 9, 12 and 12. The first joint 6 is provided on top of the support rod 1d and one of the straight arms 12, 12 extends between the first and second joints 6 and 7. It is to be noted that this arm 12 is pivotally connected to the first joint 6 so that the free end of this arm 12 may be moved up and down with the first joint 6 as a pivot and may be rotated around the support rod 1d. The other arm 12 extends between the second and third joints 7 and 8, and the two arms 12, 12 are pivotally connected through the second joint. Similarly, the arms 12 and 9 are pivotally connected through the third joint 8. With this structure, the multi-joint arm assembly 5 may be bent flexibly so as to bring the tip end of the arm 9, which serves as a hand piece and thus may be grabbed by a hand of the operator, to any desired location with any desired orientation. The multi-joint arm assembly 5 also includes a weight 13 located opposite to the arms 12, 9 and joints 6-8 with respect to the support rod 1d so as to cancel out the weight of these elements. Thus, the weight 13 serves as a balance thereby providing increased operability to the multi-joint arm assembly 5.

Figure 2:
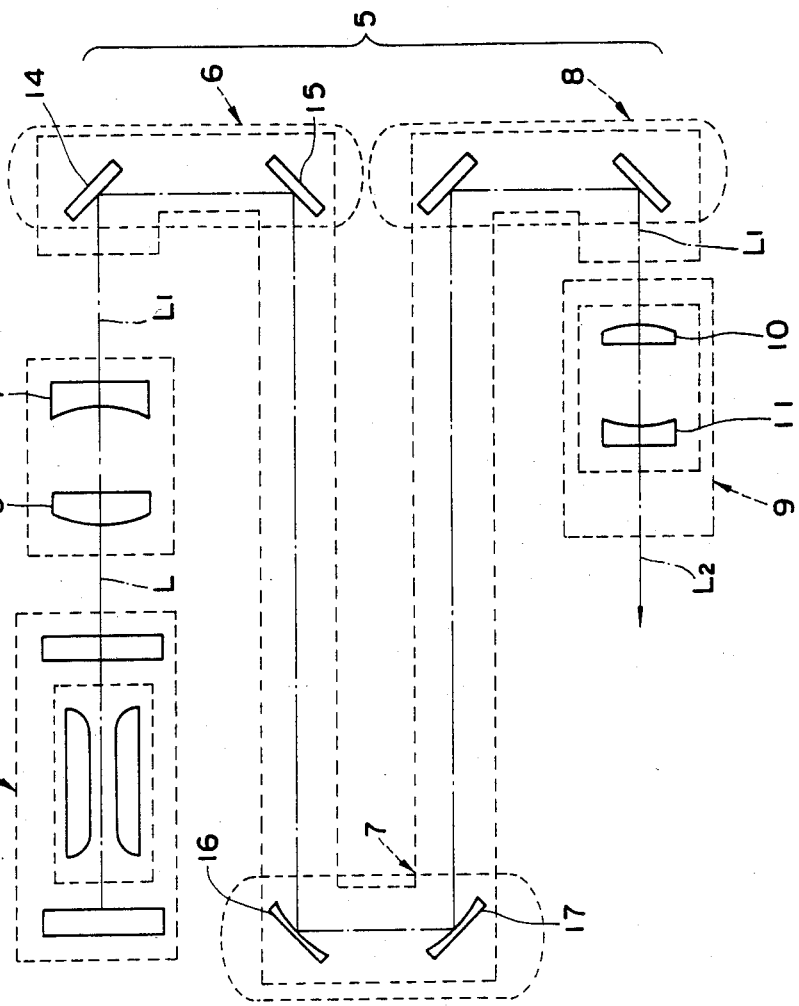
FIG. 2 is a schematic illustration showing the internal structure of the multi-joint arm of the apparatus shown in FIG. 1.

As shown in FIG. 2, the multi-joint arm assembly 5 includes a pair of inlet lenses 3 and 4 which are located to receive the laser beam L emitted from the laser unit 2 in the housing 1b. In the illustrated embodiment, the lens 3 for receiving the laser beam L from the laser unit 2 is a convex lens and the lens 4 for outputting the laser beam to the first joint 6 is a concave lens. Thus, the laser beam L emitted from the TEA type laser unit 2 is made convergent by the inlet concave lens 3, and this convergent laser beam is then collimated by the concave lens 4. Accordingly, this pair of inlet lenses 3 and 4 convert the laser beam emitted from the laser unit 2 into a narrowed and collimated laser beam L1, which is then supplied to the first joint 6. It is to be noted, that, in the case where a TEA type laser unit is used as the laser unit 2, since the laser beam emitted has a relatively large diameter, it is advantageous to provide such a pair of inlet lenses 3 and 4 to obtain the collimated laser beam L1 having a smaller diameter.

The first joint of the multi-joint arm assembly 5 includes a pair of reflecting input and output mirrors 14 and 15, respectively. The input mirror 14 is disposed in the first joint 6 so that it reflects the laser beam L1 at a right angle to the direction of advancement of the laser beam L1, and the input mirror 14 is provided to rotate around the direction of advancement of the laser beam L1 integrally with the other output mirror 15 while maintaining the condition that the laser beam L1 is reflected at right angles by the input mirror 14. The output mirror 15 receives the laser beam reflected by the input mirror 14 and reflects this laser beams at right angles. In addition, the output mirror 15 is also provided to be rotatable around the direction of advancement of the laser beam reflected by the input mirror 14. Accordingly, the input mirror 14 serves to reflect the narrow, collimated laser beam L1 in any direction in a plane perpendicular to the direction of advancement of the laser beam L1, i.e., in the horizontal plane in the illustrated embodiment since the laser unit 2 emits its laser beam vertically, and the output mirror 15 serves to reflect the laser beam reflected by the input mirror 14 in any direction in a plane perpendicular to the direction of advancement of the laser beam reflected by the input mirror 14 or in parallel with the direction of the laser beam L1, i.e., in the vertical plane in the illustrated embodiment.

On the other hand, the second joint 7 of the multi-joint arm assembly 5 includes a pair of input and output concave mirrors 16 and 17. Except for the fact that the optical elements 16 and 17 are concave and not plane mirrors as in the case of the joint 6, the input and output concave mirrors 16 and 17 of the second joint 7 are similar to the input and output plane mirrors 14 and 15 of the first joint 6. That is, the input concave mirror 16 receives the laser beam from the first joint 6 and reflects the laser beam at right angles, and the input concave mirror 16 is rotatable with respect to the optical axis of the laser beam supplied from the first joint 6 while keeping the condition of reflecting the laser beam at right angles. The output concave mirror 17 is provided so that it can rotate around the optical axis of the laser beam reflected by the input concave mirror while keeping the condition of reflecting the incoming laser beam at right angles. The second joint 7 includes a pair of concave mirrors 16 and 17 instead of a pair of plane mirrors as in the first joint 6 because the laser beam emitted from the TEA type laser unit 2 is diffusible in multimode and the pair of concave mirrors 16 and 17 serves to maintain the laser beam L1 to be collimated. Thus, if the laser beam is not strongly diffusible, the concave mirrors 16 and 17 may be replaced by plane mirrors.

The third joint 8 also includes a pair of input and output mirrors and is structurally identical to the first joint 6. Thus, the hand piece element 9 receives the collimated laser beam L1 as reflected by the pairs of mirrors at the respective joints, and the hand piece element 9 may be moved to any location within its reach and may take any desired orientation.

The end most arm or hand piece element 9 includes a pair of input and output optical elements 10 and 11 which are designed to control the laser beam by converting the laser beam L1 into a laser beam L2 which has an energy density suitable for treatment of an infected portion of a body. In the illustrated embodiment, the laser beam L2 is suitable for application to a part of a person's skin affected by dermatophytosis. For this purpose, the input optical element 10 includes a convex lens which makes the incoming laser beam L1 convergent, and the output optical element 11 includes a concave lens 11 which receives the convergent laser beam from the input convex lens 10 and converts the convergent laser beam into the collimated laser beam L2, which is then applied to a desired portion of a body. In the case of application to treatment of athlete's foot, the energy density of the laser beam L2 is preferably at 2

Joules/cm$^2$ or more and the laser beam L2 having this energy density is applied to an affected part for a predetermined time period of 10 milliseconds or less at least once.

Thus, with the present apparatus having the multi-joint arm assembly 5, the laser beam emitted from the laser unit 2 is first narrowed and collimated by the pair of inlet optical elements 3 and 4; and, after passing through the joints 6 through 8, the laser beam L1 is again narrowed and collimated by the pair of outlet optical elements 10 and 11, thereby providing the laser beam L2 having an energy density suitable for use in application to an infected portion of a body, such as a part affected by dermatophytosis. In this manner, since the laser beam L emitted from the laser unit 2 is converted into the narrowed and collimated laser beam L1 by the pair of inlet optical elements 3 and 4 provided at the inlet section of the multi-joint arm 5, the arms 12, 12 and the joints 6 through 8 may be made smaller in size and thus light in weight, which would contribute to increasing the maneuverability of the multi-joint arm assembly 5. Alternatively, instead of providing the pair of inlet optical elements 3 and 4, the pair of mirrors 14 and 15 of the first joint 6 may be replaced by a pair of concave mirrors which function to convert the laser beam L emitted from the laser unit 2 into the narrowed laser beam L1.

Figure 3:
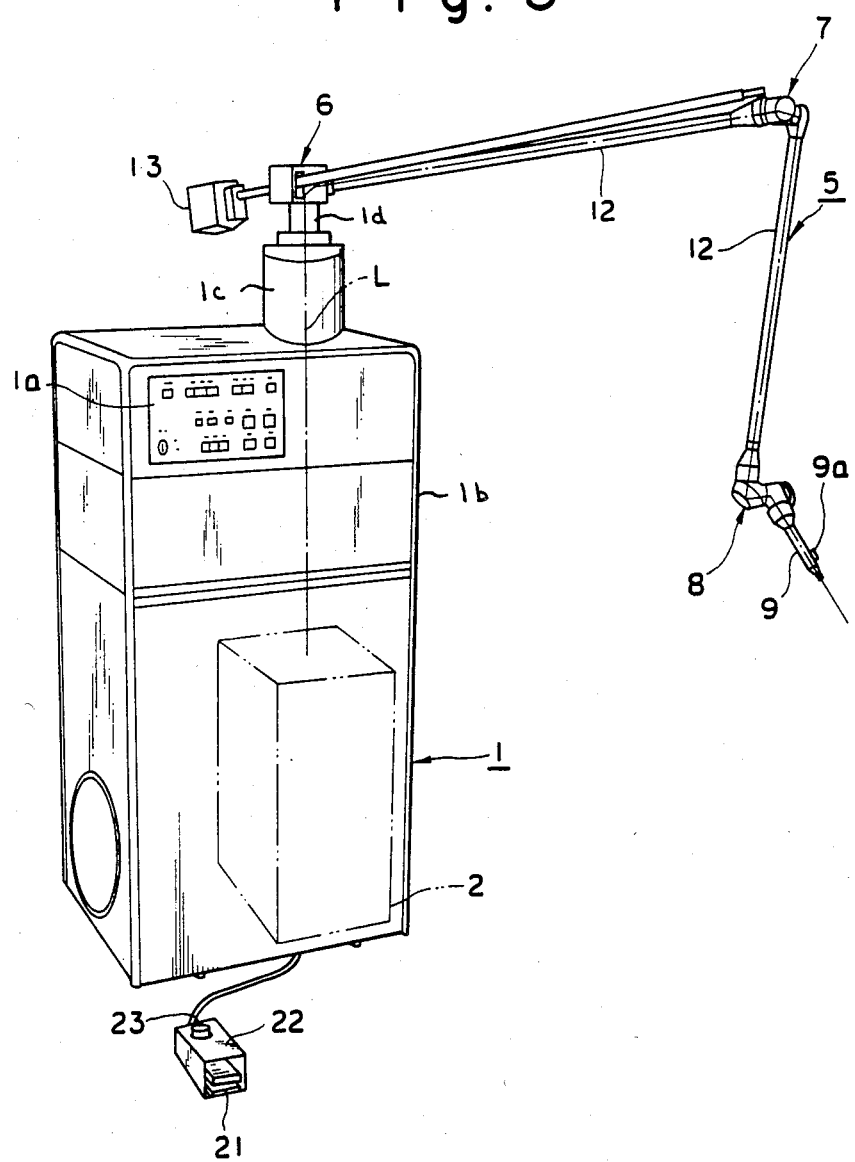
FIG. 3 is a schematic, perspective view showing another embodiment of the apparatus modified to incorporate a safety feature.

Referring now to FIG. 3, there is schematically shown a laser-applied athlete's foot treatment apparatus constructed in accordance with another embodiment of the present invention. The apparatus shown in FIG. 3 is similar to the one shown in FIG. 1, so that like numerals are indicated by like elements. As shown in FIG. 3, the laser unit 2 is contained standing upright in the housing 1b of the apparatus 1. Preferably, use is made of laser units capable of emitting a laser beam whose wavelength is in the infrared region or 0.7 microns or more, such as CO$_2$ gas laser or YAG laser. In the illustrated embodiment, use is made of a pulsed, CO$_2$ gas TEA type laser as the laser unit 2. The multi-joint arm assembly 5 has the structure shown in FIG. 2 and described above. In the present embodiment, the hand piece element 9, which may be grabbed by a hand of the operator, is provided with a depression type switch 9a, which normally takes an off position by means of a spring (not shown) and which takes an on position when depressed. Thus, the emission of laser beam L can be controlled by operating the hand switch 9a.

As shown in FIG. 3, the present apparatus is also provided with a foot switch 21 connected to the laser unit 2. The foot switch 21 is housed in a box case 22 and is normally biased upward to take its off position. Thus, the foot switch 21 turns on when the operator steps on it. It is so structured that the laser beam L is emitted from the laser unit 2 only when the hand switch 9a is operated while the foot switch 21 is depressed. Thus, a double switch structure is applied to the present embodiment, and such a structure is superior to the operation controlled only through the control panel 1a. It should also be noted that the foot switch 21 is housed in the box case 22 which substantially encloses the foot switch 22 thereby eliminating the possibility of unnecessarily operating the foot switch 21. On top of the box case 22 is provided an emergency halt switch 23 which causes the entire operation of the present apparatus to come to a halt immediately under any condition when it is depressed. Once this emergency halt switch 23 has been depressed, the laser unit 2 will not operate even if the hand and foot switches 9a and 21 are turned on at the same time unless a main switch in the control panel 1a is again depressed.

Figure 4:
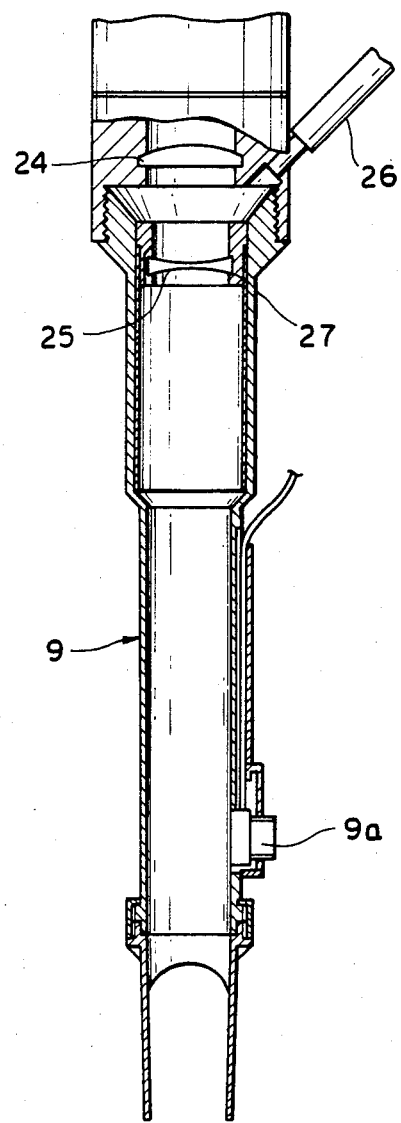
FIG. 4 is a schematic, cross-sectional view showing the detailed structure of the free end portion of the multi-joint arm of the apparatus.

FIG. 4 shows in cross section the detailed structure of the hand piece element 9 which is the endmost element of the multi-joint arm assembly 5. As shown in FIG. 4, the hand piece element 9 is provided with a convex lens 24 and a concave lens 25 which correspond to the outlet optical elements 10 and 11 shown in FIG. 2, respectively. The hand piece element 9 is also provided with a gas supplying tube 26 which is so provided to supply a predetermined gas to the space defined between the two lenses 24 and 25 thereby removing heat from both of the lenses 24 and 25. It is to be noted that a holder 27 mounted in the hand piece element 9 for mounting the concave lens 25 in position is provided with a passage for allowing the gas supplied into the space between the lenses 24 and 25 to escape to the atmosphere through an end opening of the hand piece element 9. Although not shown, it should be understood that the gas supplying tube 26 is fluidically connected to a gas source through an electromagnetic valve provided inside of the housing 1b, and the electromagnetic valve is set open only when the foot switch 21 is depressed thereby allowing the gas to flow into the space defined between the lenses 24 and 25.

With this structure, when the operator steps on the foot switch 21, the electromagnetic valve (not shown) is set open thereby supplying the cooling gas to the space between the lenses 24 and 25, and, under the condition, when the hand switch 9a is depressed or turned on with the free end of the hand piece element 9 directed to an infected part of a body, such as a part of a person's body affected by dermatophytosis, the laser beam L2 having a desired energy density is applied to the infected part. On the other hand, if the hand switch 9a is accidentally depressed without the foot switch 21 having been depressed, no laser beam is emitted from the hand piece element 9. In this manner, the present apparatus has an increased safety feature.

In the simplest embodiment, the hand switch 9a and the foot switch 21 are connected in series. In the present embodiment, however, the hand and foot switches 9a and 21 are connected to a microcomputer mounted inside of the housing 1b, and the microcomputer supplies an activation signal to the laser unit 2 when it has detected the condition that both of the hand and foot switches 9a and 21 are depressed at the same time. In this connection, the overall control system of the present apparatus in shown in block form in FIG. 5. As shown, both the hand and foot switches 9a and 21 are connected to a controller 31, which is mounted inside of the housing 1b and includes the microcomputer, and the controller 31 is connected to receive power from a power supply 30 also mounted inside of the housing 1b and to supply an activation signal to the laser unit 2. A laser beam emitted from the laser unit 2 is output as a laser output through the light-guide path defined by the multi-joint arm assembly 5. The provision of a microcomputer in the controller 31 is advantageous because it can store a program which provides operating instructions at the control panel 1a to the operator. That is, in the preferred embodiment, once the hand switch 9a has been depressed together with the depression of the foot switch 21, even if the depression of the hand switch 9a is released thereafter, the controller 31 can apply the irradiation of laser beam at a predetermined time sequence, e.g., four steps of irradiation at the rate of twice per second, in accordance with the program stored and the data input by the operation through the control panel 1a. In this case, there is no need to depress the hand switch 9a each time the irradiation of laser beam is to be carried out excepting the very first step. On the other hand, if the depression of the foot switch 21 is released, the controller 31 sends a termination signal to terminate the operation immediately even if the treatment is in progress.

While the above provides a full and complete disclosure of the preferred embodiments of the present invention, various modifications, alternate constructions and equivalents may be employed without departing from the true spirit and scope of the invention. Therefore, the above description and illustration should not be construed as limiting the scope of the invention, which is defined by the appended claims.

What is claimed is:

1. Apparatus for carrying out treatment by a laser beam, comprising:
    a housing;
    a gas laser unit of the TEA type mounted in said housing for emitting a laser beam having a predetermined wavelength;
    a multi-joint arm assembly movably mounted on said housing for leading said laser beam emitted from said laser unit to an output end thereof as guided therethrough, said multi-joint arm assembly comprising:
        a plurality of arms and a plurality of joints, each of said joints movably connecting ends of corresponding two of said plurality of arms;
    a reflecting means for reflecting said laser beam from one of the two corresponding arms to the other;
    optical adjusting means for collimating and narrowing the laser beam width disposed in a passage of said laser beam between said laser unit and said output end of said multi-joint arm assembly and for adjusting said laser beam such that it has a predetermined energy density when output through said output end; and wherein
    said optical adjusting means includes a pair of input and output optical elements, whereby said input optical element makes the laser beam convergent and said output optical element collimates said convergent laser beam from said optical system.

2. A laser-applied treatment apparatus, as in claim 1 in which said multi-joint arm assembly further includes:
    a hand piece element which is provided with an output end for application of said laser beam to a desired portion of a body and which may be grabbed by an operator; and
    first switching means mounted on said hand piece for controlling the operation of said laser unit.

3. The apparatus of claim 2 further comprising second switching means for controlling the operation of said laser unit, said second switching means being operatively associated with said first switching means such that said first switching means is enabled to control the operation of said laser unit as long as said second switching means is being operated.

4. The apparatus of claim 3 wherein said first and second switching means are connected in series.

5. The apparatus of claim 3 further comprising controlling means which is operatively connected to said laser unit and to both of said first and second switching means, said controlling means includes a microcomputer which supplies an activation signal in accordance with the conditions of said first and second switching means.

6. The apparatus of claim 5 wherein said microcomputer stores a program which automatically controls the operation of said laser unit such that said laser unit is operated for the number of times set by the operator in a timed sequence once said first switching means has been operated by the operator if said second switching means is kept operated.

7. The apparatus of claim 6 wherein said controlling means terminates the operation immediately upon detecting the fact that said second switching means has been deactivated.

8. The apparatus of claim 1 wherein said optical adjusting means includes a convex lens for making said laser beam convergent and a concave lens for making said convergent laser beam collimated, whereby said laser beam becomes narrowed in cross sectional area.

* * * * *